US006963062B2

United States Patent
Cyr et al.

(10) Patent No.: US 6,963,062 B2
(45) Date of Patent: Nov. 8, 2005

(54) METHOD FOR MULTIPLEXED OPTICAL DETECTION INCLUDING A MULTIMODE OPTICAL FIBER IN WHICH PROPAGATION MODES ARE COUPLED

(75) Inventors: Douglas R. Cyr, Livermore, CA (US); Roger L. Farrow, Pleasanton, CA (US)

(73) Assignee: Eksigent Technologies, LLC, Livermore, CA (US)

( * ) Notice: Subject to any disclaimer, the term of this patent is extended or adjusted under 35 U.S.C. 154(b) by 199 days.

(21) Appl. No.: 10/410,314

(22) Filed: Apr. 7, 2003

(65) Prior Publication Data

US 2004/0196459 A1 Oct. 7, 2004

(51) Int. Cl.⁷ .............................................. G02B 6/42
(52) U.S. Cl. .......................... 250/227.25; 250/227.28
(58) Field of Search ....................... 250/227.25, 227.28, 250/227.14, 227.21, 227.22, 227.11, 227.12; 385/32, 39, 27; 356/477

(56) References Cited

U.S. PATENT DOCUMENTS

| 4,229,067 A | 10/1980 | Love |
| 4,360,372 A | 11/1982 | Maciejko ................. 65/4.21 |
| 4,714,314 A | 12/1987 | Yang et al. |
| 4,811,172 A | 3/1989 | Davenport et al. ........... 362/61 |
| 4,907,851 A | 3/1990 | Marhic |
| 4,910,539 A | 3/1990 | Mathis et al. |
| 5,058,985 A | 10/1991 | Davenport et al. ......... 385/115 |
| 5,077,814 A | 12/1991 | Shigematsu et al. .......... 385/24 |
| 5,199,091 A | 3/1993 | Davenport et al. ........... 385/39 |
| 5,259,056 A | 11/1993 | Davenport et al. ......... 385/115 |
| 5,341,445 A | 8/1994 | Davenport et al. ........... 385/39 |
| 5,367,590 A | 11/1994 | Davenport et al. ........... 385/39 |
| 5,375,387 A | 12/1994 | Davenport ................. 385/353 |
| 5,446,280 A | 8/1995 | Wang et al. ............ 250/227.23 |
| 5,479,545 A | 12/1995 | Davenport et al. ........... 385/43 |
| 6,208,678 B1 * | 3/2001 | King ............................ 372/72 |
| 6,542,231 B1 | 4/2003 | Garrett ....................... 356/246 |

FOREIGN PATENT DOCUMENTS

| DE | 43 09 389 A1 | 9/1993 |
| JP | 58-14108 | 1/1983 |
| JP | 6-18751 | 1/1994 |

OTHER PUBLICATIONS

Operator's Guide, Waters 2488 Multichannel Absorbance Detector with MassLynx Control, Operator's Guide, 71500248802 Revision A, Waters Corporation, Milford, MA (2001), in particular Ch. 1 ('2488 Detector Theory of Operation'), pp. 1–9.

Federal Standard 1037C, Telecommunications: Glossary of Telecommunications Terms, selective pages.

(Continued)

Primary Examiner—Que T. Le
(74) Attorney, Agent, or Firm—Sheldon & Mak; Jeffrey G. Sheldon (57) ABSTRACT

A method for multiplexed optical detection includes: imaging light onto an input face of a first optical fiber, wherein the first optical fiber is a multimode optical fiber; inducing coupling among the propagation modes of the light in the first optical fiber; coupling an output face of the first optical fiber to input faces of multiple individual second optical fibers in a multi-fiber bundle, wherein each output face of the individual fibers emits substantially similar light; and detecting one or more properties of one or more fluids, including analytes that may be present, with the light emitted from at least one of the second optical fibers. The second optical fibers can be a part of an optical detector that is part of a high performance liquid chromatography system, which can be located in a substrate.

29 Claims, 3 Drawing Sheets

OTHER PUBLICATIONS

Hazan, J.–P. et al., Characterizing optical fibres; a test bench for pulse disperson, Philips tech. Rev. 36, pp. 211–216, 1976, No. 7.

Ikeda, Masahiro et al., Multimode optical fibers: steady state mode exciter, Applied Optics, vol. 15, No. 9, Sep. 1976, pp. 2116–2120.

Ikeda, Masahiro et al., Mode scrambler for optical fibers, Applied Optics, vol. 16, No. 4, Apr. 1977, pp. 1045–1049.

Tateda, Mitsuhiro et al., Mode conversion in bent step index multimode fibers, Applied Optics, vol. 15, No. 10, Oct. 1976, pp. 2308–2310.

* cited by examiner

METHOD FOR MULTIPLEXED OPTICAL DETECTION INCLUDING A MULTIMODE OPTICAL FIBER IN WHICH PROPAGATION MODES ARE COUPLED

BACKGROUND

Optical detection methods are frequently employed in analytical instruments for sensitive and species-specific detection of chemical compounds. Optical detection is particularly well suited for analytical techniques such as high performance liquid chromatography (HPLC). HPLC has been used for many years as a means of separating, identifying, purifying and quantifying components of often-complex mixtures. HPLC is an important tool used by biotechnological, biomedical, and biochemical research as well as in the pharmaceutical, cosmetics, energy, food, and environmental industries.

Typically, the optical systems associated with HPLC detectors use a series of lenses and mirrors to collect and propagate light from a source through free space to a flow cell. Fluid containing analytes that have been separated by elution through a chromatographic column flows through this cell. Light not absorbed after passing through this cell strikes a light detector containing one or more photosensitive elements.

Propagation of light through free space has certain disadvantages. Specifically, for satisfactory operation, the mechanical stability of each optical component has to be extremely high to ensure the optical path length is faithfully maintained. In addition, beam tubes often have to be used to alleviate the susceptibility to air currents, which can change the local refractive index and slightly bend light rays, contributing uncertainties (noise) in sensitive measurements. Lastly, losses of light intensity occur due to Fresnel reflections at each air-glass interface due to the sudden change in refractive index.

These disadvantages can be largely avoided by propagating light through optical fibers. Using an optical fiber to transmit light has additional advantages. Doing so minimizes the use of optical elements such as collimating lenses and reflectors, particularly when path lengths are extended. Further, optical fibers are flexible, allowing the primary light source to be located in places not feasible if the light were being propagated through free space. Lastly, optical fibers can transmit light with little or no loss of intensity, even over extended distances.

Because the location of the primary light source relative to the optical detector is less important when using optical fiber and because a single primary light source can illuminate multiple optical fibers simultaneously, a single source of light can be directed to a number of optical detectors simultaneously via multiple optical fibers. This will be useful in parallel HPLC systems, which are currently on the verge of introduction to the marketplace and will further increase sample processing speed in analytical instrumentation.

One example of a prior art device where a single primary light source illuminates multiple optical fibers is the Waters Corporation Model 2488 Multichannel Absorbance Detector. According to its Operator's Guide, Waters 2488 Multichannel Absorbance Detector with MassLynx Control, Operator's Guide, 71500248802 Revision A, Waters Corporation, Milford, Mass. (2001), the detector uses a deuterium lamp followed by a combination of mirrors and a grating to select light within a single wavelength band and to focus this light directly onto the input ends of eight optical fibers. The input ends of the eight short optical fibers are arranged in two parallel rows of four, one row offset from the other by half of a fiber diameter for closer packing. The eight fibers transmit the wavelength-selected light that is then focused through respective sample detection cells and onto associated detection photodiodes. This system is a hybrid one, combining optical fibers with a number of free space optical components. There are also a number of other commercially available optical detection systems incorporating optical fibers into their design.

As with many other single wavelength instruments, a beam splitter located between the optical fibers and the deuterium lamp directs some of the single wavelength light into a reference photodiode. This allows the output of the deuterium lamp to be monitored independent of absorption by any sample. In theory, when analyzing data from the sample detection cells, compensation can then be made for any fluctuations in the intensity of the light from the lamp.

Incoherent light sources, such as a deuterium lamp, are often treated theoretically as point sources, i.e. filling no volume. In reality they do have a finite spatial extent and the intensity and spectral distribution of the light emanating from different areas of the incoherent light source volume can vary strongly. For this reason, if no special precautions are taken, the intensity of light delivered to each individual optical fiber in a bundle (as well as the light directed to the reference photodiode) can differ strongly. If the alignment varies in time, even slightly, or there is a power fluctuation causing a change in the intensity of light, the variation will be different from fiber to fiber and from fibers to reference. This means that even slight changes in the relative position of the source and the multi-fiber bundle, or diffraction of the light beam by fluctuating air currents, will cause variations in signal intensity from the individual detectors, and the variations will not be correctable or normalizable.

Furthermore, it is often desirable to analyze a sample using broadband detection, i.e. detecting at a whole range or spectrum of wavelengths simultaneously. The use of mirrors or lenses to collect and focus light onto the input ends of multiple optical fibers can exacerbate the spatial and (if broadband sources are used) chromatic inhomogeneities of the source light distribution, thereby increasing the non-uniformities between the output of each of the individual fibers and the light directed to the reference photodiode. The Waters Corporation Model 2488 uses a grating to select only a single narrow wavelength band. However, if its design were modified to attempt to focus multiple wavelengths of light onto the input ends of the optical fibers the outputs of the individual fibers and light directed to the reference photodiode would be likely to also vary in spectral distribution.

To accurately compensate for the fluctuations in the intensity of the light from the incoherent light source, the light delivered to each optical fiber and the light directed to the reference diode must be substantially similar in intensity and spectral characteristics. "Similar" here refers to strictly proportional relationships between the profiles, both spatial and spectral, of the light delivered to each fiber and to the reference photodiode. It is also important that the proportionality constants relating these profiles remain stable so that they can be determined by calibration between measurements. For example, if one fiber transmits 1000 analog-to-digital-converter (ADC) counts at 254 nm and the other transmits 1100 ADC counts at 254 nm, then if the source lamp fluctuates upward to 1010 ADC counts as transmitted by the first, the second should transmit 1111 ADC counts.

If a broadband light source is used with the goal of broadband detection, the spectral characteristics of the light emanating from different areas of the source volume will also vary and chromatic aberrations will result from variations in the imaging of light of different wavelengths.

Alternatively, if the light source is a laser, the coherence properties of the laser light can cause only a limited number of waveguide propagation modes to be launched within the optical fibers. Because of this, the output is not spatially uniform but exhibits pronounced intensity fluctuations referred to as "speckle."

Accordingly, there is a need in the art for a method for multiplexed optical detection wherein one light source is coupled to multiple optical fibers in such a way that the output of the optical fibers is substantially insensitive to movement of the fibers and substantially similar and homogeneous in terms of intensity and spectral profiles, and wherein changes in illumination of the multiple optical fibers by the light source results in uniform changes to the output intensity and spectral profiles of each output fiber.

SUMMARY

The present invention satisfies this need. The present invention provides a method for multiplexed optical detection comprising the steps of: (a) illuminating the input face of a first optical fiber so that light enters the first optical fiber, wherein the first optical fiber is a multimode optical fiber; (b) inducing mode coupling of the light in the first optical fiber; (c) coupling the output face of the first optical fiber to input faces of multiple individual second optical fibers in a multi-fiber bundle, wherein each output face of the individual second optical fibers emits substantially similar light; and (d) detecting one or more properties of one or more fluids with the light emitted from at least one of the second optical fibers. The step of inducing mode coupling can also result in mode filtering, which allows the output of each of the fibers in the multi-fiber bundle to be insensitive to movement of the fiber.

The light from the light source can be incoherent or coherent, continuous or pulsed. The second optical fibers can be multimode fibers, single-mode fibers or a combination of the two. At least a portion of one or more of the second optical fibers can be located in a substrate or be coupled to one or more fibers that have a portion located in a substrate. Light emitted from one of the second optical fibers can be directed to a light detector so that qualities of the light imaged onto the input face of the first optical fiber and light emitted from the other second optical fibers can be monitored.

The first optical fiber can be coupled to a light guide, multiple light guides, or a combination of light guides and optical fibers instead of the second optical fibers. The light guide can be located at least partially in a substrate and the light guide can be comprised of a dielectric medium having a refractive index higher than the refractive index of the substrate.

The present invention also provides multiple substantially similar secondary light sources for use in an optical detection comprising: (a) a primary light source; (b) a first optical fiber having an input face and an output face, wherein the first optical fiber is a multimode optical fiber; wherein light from the light source is imaged onto the input face of the first optical fiber; and wherein the light in the first optical fiber has modes and the modes are coupled, allowing an equilibrium distribution among lossless propagating modes to be substantially formed; (c) a plurality of second optical fibers in a multi-fiber bundle, each second optical fiber having an input face and an output face, wherein the input faces are coupled to the output face of the first optical fiber and wherein the output faces of the second optical fibers emit substantially similar light. One of the multiple substantially similar secondary light sources can serve as a reference light source.

The present invention further provides a high performance liquid chromatography system comprising: (a) a chromatographic column having a fluid outlet; and (b) an optical detector comprising: (i) a light source; (ii) a light detector; and (iii) a flow path located between the light source and the light detector and in fluid communication with the fluid outlet; wherein the light source is comprised of one or more of the multiple substantially similar secondary light sources.

DESCRIPTION

This disclosure describes a method for multiplexed optical detection wherein one light source is coupled to multiple optical fibers in such a way that the output of the optical fibers is substantially insensitive to movement of the fibers and substantially similar and homogeneous in terms of intensity and spectral profiles, and wherein changes in illumination of the multiple optical fibers by the light source results in uniform changes to the output intensity and spectral profiles of each output fiber. Because the individual multiple fibers carry light, which is substantially insensitive to movement of the fibers and has substantially similar characteristics, any one fiber can be used as a reference for the rest.

Figure 1:
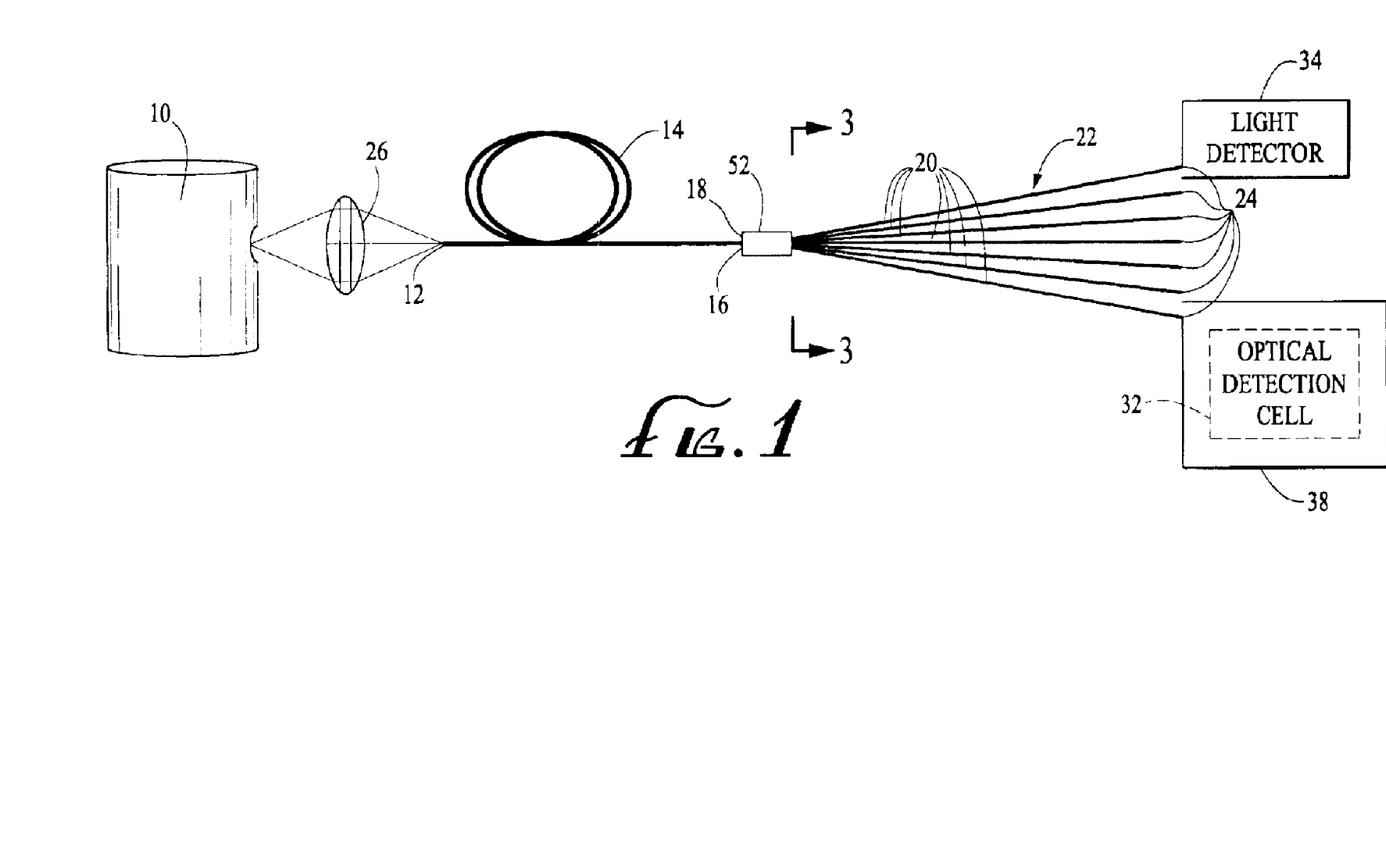
FIG. 1 is a schematic diagram of multiplexed optical detection according to the present invention.
Figure 2:
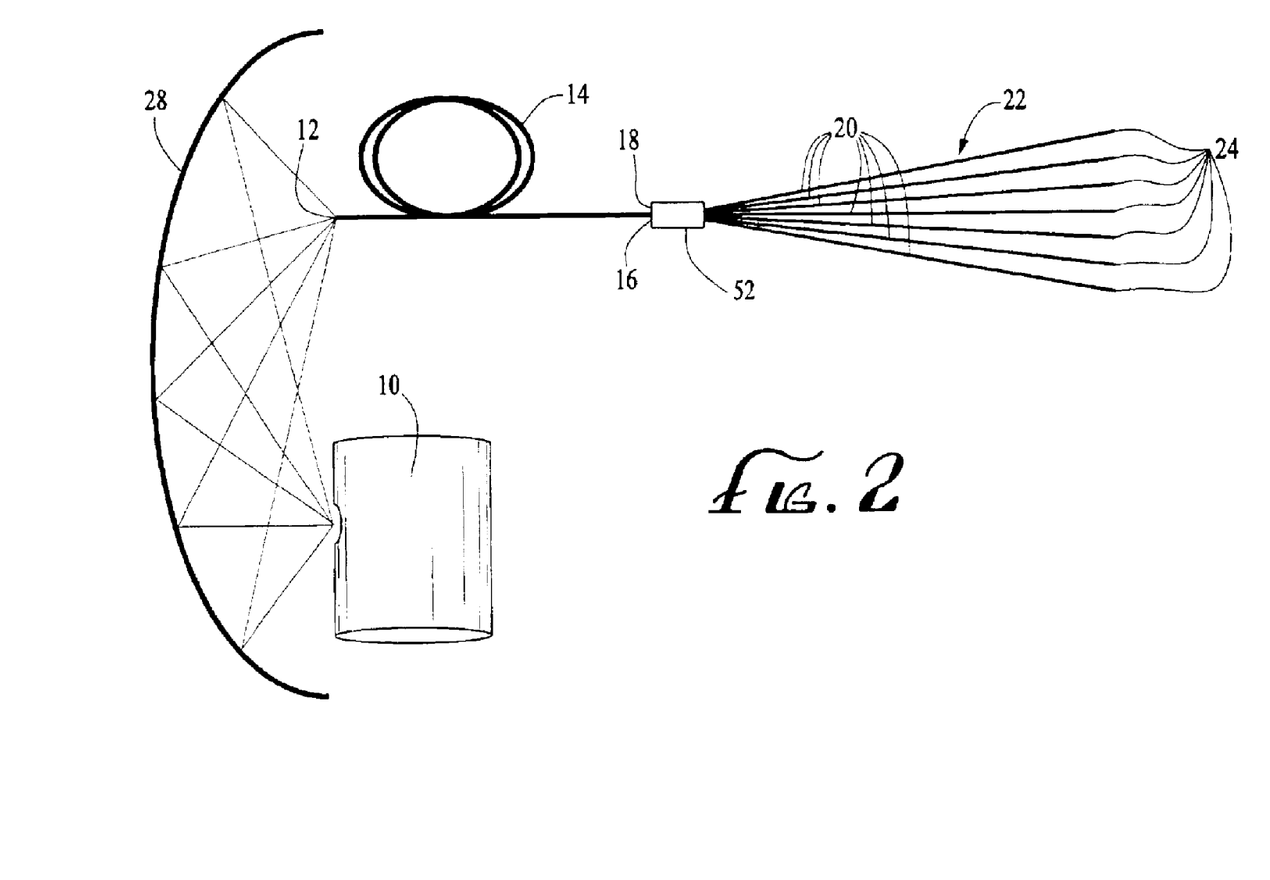
FIG. 2 is a schematic diagram of a second embodiment of multiplexed optical detection according to the present invention.

Referring to FIGS. 1 and 2, a method for multiplexed optical detection according to the present invention includes illuminating an input face 12 of a multimode optical fiber 14, also described herein as the first optical fiber, with light from a light source 10 so that light enters the first optical fiber. Coupling among the propagation modes of the light in the first optical fiber 14 is induced. An output face 16 of the multimode optical fiber 14 is coupled to input faces 18 of individual fibers 20 in a multi-fiber bundle 22. The individual fibers 20 in the multi-fiber bundle 22 are also described herein as second optical fibers 20. Each output face 24 of the second optical fibers 20 emits substantially similar light distributions, thus, providing multiple, substantially similar light sources for multiplexed optical detection schemes. The multiple, substantially similar light sources are free of any spatial and chromatic inhomogeneities of the original, primary light source 10. One or more properties of one or more fluids, including what analyte or analytes the fluid contains and at what concentration, can be detected with the light emitted from the second optical fibers 20. Any of the second optical fibers 20 can serve as a source reference for the light supplied by the other second optical fibers when used in optical detection systems that compensate for light source fluctuations.

The light imaged onto the multimode optical fiber 14 can be pulsed or continuous, coherent or incoherent. The light source 10 can be a deuterium lamp or other discharge or arc lamp, an incandescent lamp, a hollow cathode lamp, a light emitting diode, a laser diode, a Vertical Cavity Surface Emitting Laser "VCSEL", or any other laser-based source, or any other light source known in the art.

The light source 10 is preferably imaged onto the input face 12 of the first optical fiber so that as much light as possible enters the first optical fiber 14 within the acceptance angle defined by the numerical aperture of the fiber. The light can be imaged onto the input face 12 of the first optical fiber 14 using curved reflectors, such as elliptical mirrors, or a lens or a series of lenses or a combination of any number of reflectors and lenses, or any way known by those skilled in the art.

Alternatively, the first optical fiber 14 can be placed as near as possible to the source 10 and light can enter the first optical fiber 14 directly, without the benefit of any optical devices. This arrangement, where no optical devices are used, works better with laser sources because of their highly directional output. Using no optical devices provides much less collected light intensity when incoherent sources are used.

FIGS. 1 and 2 illustrate two common methods of collecting and imaging light. In FIG. 1, light from the source 10 is collected by a lens assembly 26 and imaged onto the input face of the first optical fiber 12. In FIG. 2, light from the source 10 is collected by an elliptical mirror 28 and imaged onto the input face 12 of the first optical fiber 14. All of the rays of light that are directed onto the input face 12 of the first optical fiber 14 and are within the acceptance angle of the first optical fiber will, save for a small loss due to Fresnel reflection at the fiber's input face, enter the fiber.

Mode coupling causes the distribution of power initially present in the propagation modes of the first optical fiber 14 to undergo redistribution, resulting in a modified distribution substantially similar to the equilibrium mode distribution, characterized by uniform output, which is substantially independent of input spatial and chromatic inhomogeneities. Mode coupling causes the output of the multimode fiber 14 to be substantially homogenized. The first optical fiber 14 has substantially similar output in terms of intensity, spectral distribution and numerical aperture at any point on its output face 16.

Mode coupling of the light in the first optical fiber 14 can be induced simply by using a sufficiently long length (1–2 km) of multimode optical fiber. However, it is usually desirable to use other mode coupling techniques in order to minimize the length of fiber used for this process. For example, the first optical fiber 14 can be looped to cause mode coupling. Alternatively, the first optical fiber 14 can be mounted in such a way as to cause microbending, which also causes mode coupling. Coupling a sharply focused laser beam into a length of multimode step index fiber having the same numerical aperture results in mode coupling. Also, etching the end of the first optical fiber 14 results in a structure that serves as a diffuser and a mode exciter for the initial low order modal distribution launched by a laser source, resulting in mode redistribution. Fusing a length of graded index fiber between two pieces of step index fiber will also cause mode coupling. Other methods of mode coupling exist, any method of which can be used.

Preferably, mode filtering also occurs to the light in the first optical fiber. Mode filtering removes the highest order modes, which are characterized by relatively lower angles of incidence between the mode propagation vector and the vector normal to the fiber-cladding interface and which are most likely to be affected by repositioning of the fibers if they are allowed to remain. The highest order modes can radiate out of the fiber if the fibers are moved because the angles of incidence of the highest order modes can fall below the critical angle when a fiber is bent, causing loss of light from these modes. It is undesirable to have to maintain the second optical fibers 20 in a perfectly fixed position so that they do not bend. By stripping out or filtering such high-order modes from the mode distribution entering the second optical fibers 20, the latter are able to transmit the distribution without substantial modification should bending occur. As a result, there is a significant advantage in using looping or microbending in the first fiber 14 to induce mode coupling, as this method simultaneously filters or strips undesired higher-order modes from the initial distribution. If further mode filtering is desired, the second optical fibers 20 can also be looped or subjected to microbending in an identical manner to preserve uniformity.

Figures 3, 4:
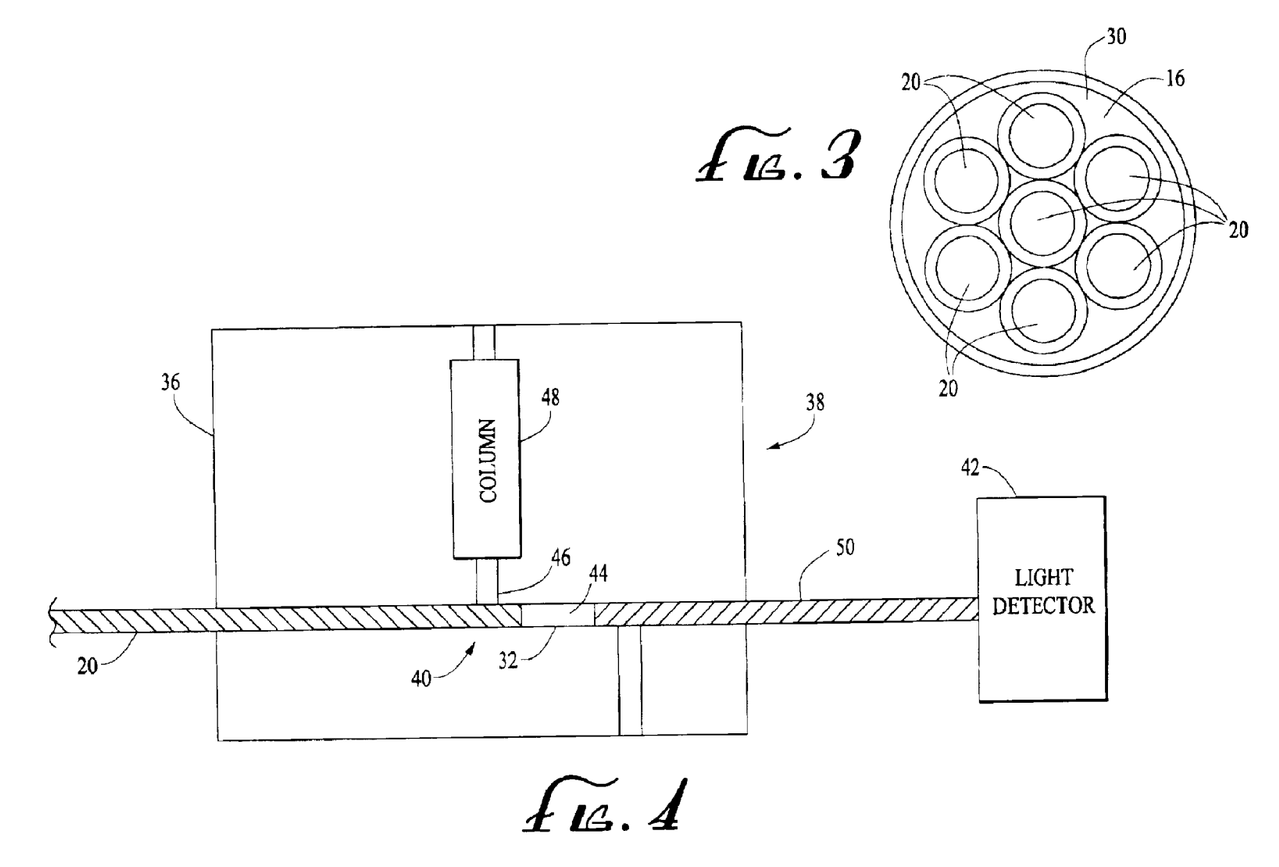
FIG. 3 is a cross-section view of the junction of the first optical fiber with the second optical fibers taken at line 3—3 of FIG. 1.
FIG. 4 is a cross-sectional view of an HPLC system located in a substrate in accordance with the present invention.

The output face 16 of the first optical fiber 14 is coupled, preferably butt-coupled, to the second optical fibers 20 in a multi-fiber bundle 22 such that the multi-fiber bundle is centered within the area of the light-guiding core 30 of the first optical fiber, as shown in FIG. 3. This can be accomplished using a union coupler 52. The union coupler 52 is hollow and holds the second optical fibers 20 together and immediately adjacent to the first optical fiber 14 while allowing for separation of the second optical fibers from the first optical fiber when desired. For cases when the optical fibers are transmitting wavelengths in the visible range, it would advantageous to use an appropriate index-matching fluid between the output face 16 of the first optical fiber 14 and the input faces 18 of the second optical fibers 20 to avoid losses due to Fresnel reflections at the air-glass interface in case the union did not provide for perfect contact between fiber faces.

Preferably the diameter of the first optical fiber 14 is large relative to the second optical fibers 20 so that the light guiding core of the entire bundle 22 can fit with the diameter of the light guiding core 30 of the first optical fiber as shown in FIG. 3. For example, in FIG. 3, seven second optical fibers 20 are packed in a hexagonal configuration having a diameter less than the first optical fiber 14. Each of the seven second optical fibers 20 can have a 159 $\mu$m core and a 175 $\mu$m cladding diameter. The first optical fiber can have a 600 $\mu$m core 30 and a 660 $\mu$m cladding diameter. Because the 600 $\mu$m core 30 of the first optical fiber 14 is slightly larger than the overall diameter of the multi-fiber bundle 22, this arrangement is insensitive to small misalignments.

Preferably, each of the second optical fibers 20 in the multi-fiber bundle 22 has a numerical aperture that is substantially similar to that of the first optical fiber 14. Each of the second optical fibers 20 in the multi-fiber bundle 22 can be singlemode or multimode, step index or graded index. However, when used to transmit ultraviolet light, step index optical fibers perform substantially better than currently available graded index optical fibers.

Since each of the second optical fibers 20 in the multi-fiber bundle 22 is illuminated by light having substantially similar intensity and spectral characteristics, the output face 24 of each of the second optical fibers in the multifiber bundle can serve as a light source (referred to herein as a secondary light source) in a distinct optical detection cell 32 for multiplexed optical detection, where each of the secondary light sources are substantially similar in terms of intensity and spectral characteristics. Light emitted from the second optical fibers 20 can be used to detect one or more properties of one or more fluids. Also, light emitted from one of the second optical fibers 20 can be directed to a light detector 34 so that qualities, such as intensity and spectral characteristics, of the light imaged onto the input face 12 of the first optical fiber 14 and the light emitted from the other second optical fibers can be monitored. The light detector 34 can be a photodiode or any other light detector known in the art, including detectors that allow wavelength-dispersed detection. Further, the primary light source 10 can be moved relative to the first optical fiber 14 and the output in terms of both intensity and spectral characteristics of the second optical fibers 20 in the multi-fiber bundle 22 will change in a consistent manner.

At least a portion of one or more of the second optical fibers 20 in the multi-fiber bundle 22 can be located in a substrate 36 as shown in FIG. 4. For example, one or more of the second optical fibers 20 in the multi-fiber bundle 22 can be part of one or more HPLC systems 38 located in one or more substrates 36. Of course, the second optical fibers 20 in the multi-fiber bundle 22 can be part of an HPLC system 38 that is not located in a substrate 36. For convenience, the second optical fibers can each be coupled to a different third optical fiber that has an end located in the substrate.

An optical detector 40 in the HPLC system 38 can comprise a light source, a light detector 42, and a flow path 44 located between the light source and the light detector 42. The light source can be one of the second optical fibers 20. Optionally, one or more of the second optical fibers can be coupled to a third optical fiber, which acts as the light source. This is beneficial when the third optical fiber is glued into a substrate and it is necessary to disconnect the chip from the multifiber bundle fiber easily. The light detector 42 can be a photodiode or any other light detector known in the art, including detectors that allow wavelength dispersed detection. A fluid outlet 46 of a chromatographic column 48 can be in fluid communication with the flow path 44.

For best results, preferably, a fourth optical fiber 50 couples the detection cell 32 to the light detector 42. The second and fourth optical fibers 20 and 50, respectively, preferably extend into the flow path 44 so that the velocity of fluid flowing into the flow path is substantially uniform and the dispersion of the optical detector is reduced as disclosed in U.S. patent application entitled Microfluidic Detection Device Having Reduced Dispersion and Method for Making Same invented by Douglas R. Cyr, Roger L. Farrow and Don W. Arnold and incorporated herein by reference for any and all purposes.

Alternatively, the second optical fibers 20 can couple the first optical fiber 14 to one or more light guides. The light guides can be comprised of silica glass, with or without doping; plastic; light pipes, including those with a liquid core; or any other material known in the art.

Light emitted from the light guide or guides can be used to detect one or more properties of one or more fluids, including the presence, identity and quantity of analytes that may be present. The light guide or guides can also be located at least partially in a substrate 36 and be part of an HPLC system 38. When the light guide is located at least partially in a substrate 38, the light guide preferably has a refractive index higher than the refractive index of the substrate or the light guide has a cladding that is lower in refractive index than the core.

In one embodiment of the invention, the output from a Hamamatsu L-6999 deuterium lamp was coupled by means of an optimized pair of calcium fluoride lenses to a single 67 cm long, 600-$\mu$m core UVM step index multimode fiber having a numerical aperture (NA) of 0.22 from Polymicro Technologies (UVM refers to a modified ultraviolet-transmitting fiber). The multimode optical fiber was coiled twice in orthogonal directions, prior to entering a union coupler. The union coupler centered and butt-coupled the multimode fiber to a three-fiber bundle of 100 cm long, 200 $\mu$m core UVM step index second optical fibers also having NA=0.22. The union coupler was a SMA (connector type) to SMA mating sleeve. Each of these three 200 $\mu$m core fibers are substantially similar light sources and any of them can serve as a reference for the other two. Each of the second optical fibers was coupled to a distinct 100 $\mu$m fiber which transmitted light to and was glued in a detection cell within a substrate.

Although the present invention has been described in considerable detail with reference to certain preferred versions thereof, other versions are possible. For example, transfer optics can be used to couple light from the first optical fiber to the second optical fibers. Therefore, the spirit and scope of the appended claims should not be limited to the description of the preferred versions contained herein.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function should not be interpreted as a "means" or "step" clause as specified in 35 U.S.C. § 112.

What is claimed is:

1. A method for multiplexed optical detection comprising the steps of:
   (a) illuminating an input face of a first optical fiber so that light enters the first optical fiber, wherein the first optical fiber is a multimode optical fiber having propagation modes;
   (b) inducing coupling among the propagation modes of the light in the first optical fiber;
   (c) coupling an output face of the first optical fiber to input faces of multiple individual second optical fibers in a multi-fiber bundle, wherein each output face of the second optical fibers emits substantially similar light; and
   (d) detecting one or more properties of one or more fluids with the light emitted from at least one of the second optical fibers.

2. The method of claim 1 further comprising the step of monitoring the qualities of the light imaged onto the input face of the first optical fiber.

3. The method of claim 1 wherein the step of inducing mode coupling also induces mode filtering.

4. The method of claim 1 wherein the light entering the first optical fiber is substantially incoherent.

5. The method of claim 1 wherein the light entering the first optical fiber is substantially coherent.

6. The method of claim 1 wherein the light entering the first optical fiber is continuous.

7. The method of claim 1 wherein the light entering the first optical fiber is pulsed.

8. The method of claim 1 wherein at least a portion of one of the second optical fibers is directed to a substrate.

9. The method of claim 1 wherein at least one of the second optical fibers is a multimode fiber.

10. The method of claim 1 wherein at least one of the second optical fibers is a single mode fiber.

11. The method of claim 1 wherein light emitted from one of the second optical fibers is directed to a light detector so that qualities of the light emitted from the other second optical fibers can be monitored.

12. The method of claim 1 wherein light emitted from one of the second optical fibers is directed to a light detector so that qualities of the light imaged onto the input face of the first optical fiber can be monitored.

13. A method for multiplexed optical detection comprising the steps of:
   (a) illuminating an input face of a multimode optical fiber having propagation modes so that light enters the multimode optical fiber;
   (b) inducing coupling among the propagation modes of the light in the multimode optical fiber;
   (c) coupling an output face of the multimode optical fiber to a light guide located at least partially in a substrate; and
   (d) detecting one or more properties of one or more fluids with the light emitted from the light guide.

14. A system having multiple substantially similar secondary light sources for use in an optical detection system comprising:
   (a) a primary light source;
   (b) a first optical fiber having an input face and an output face, wherein the first optical fiber is a multimode optical fiber; wherein light from the primary light source is imaged onto the input face of the first optical fiber; and wherein the first optical fiber has propagation modes and the modes are coupled; and
   (c) a plurality of secondary optical fibers in a multi-fiber bundle, each secondary optical fiber having an input face and an output face, wherein the input faces are coupled to the output face of the first optical fiber and wherein the output faces of the secondary optical fibers emit substantially similar light to serve as secondary light sources.

15. The system similar of claim 14 wherein one of the multiple substantially similar secondary light sources serves as a reference light source.

16. A high performance liquid chromatography system comprising:
   (a) a chromatographic column having a fluid outlet; and
   (b) an optical detector comprising:
      (i) a light source;
      (ii) a light detector; and
      (iii) a flow path located between the light source and the light detector and in fluid communication with the fluid outlet; wherein the light source comprises one of the multiple substantially similar secondary light sources of a light system comprising:
   (i) a primary light source;
   (ii) a first optical fiber having an input face and an output face; wherein the first optical fiber is a multimode optical fiber; wherein light from the light source is imaged onto the input face of the first optical fiber; and wherein the first optical fiber has propagation modes and the modes are coupled; and
   (iii) a plurality of secondary optical fibers in a multi-fiber bundle, each secondary optical fiber having an input face and an output face; wherein the input faces are coupled to the output face of the first optical fiber; and wherein the output faces of the secondary optical fibers emit substantially similar light.

17. A high performance liquid chromatography system comprising:
   (a) a plurality of chromatographic columns, each column having a fluid outlet; and
   (b) a plurality of optical detectors, each optical detector comprising:
      (i) a light source;
      (ii) a light detector; and
      (iii) a flow path located between the light source and the light detector and in fluid communication with the outlet of at least one of the plurality of chromatographic columns; wherein the light source comprises one of the multiple substantially similar light sources of a light system comprising:
   (i) a primary light source;
   (ii) a first optical fiber having an input face and an output face; wherein the first optical fiber is a multimode optical fiber; wherein light from the light source is imaged onto the input face of the first optical fiber; and wherein the first optical fiber has propagation modes and the modes are coupled; and
   (iii) a plurality of secondary optical fibers in a multi-fiber bundle, each secondary optical fiber having an input face and an output face; wherein the input faces are coupled to the output face of the first optical fiber; and wherein the output faces of the secondary optical fibers emit substantially similar light.

18. A method for multiplexed optical detection comprising the steps of:
   (a) illuminating an input face of a first optical fiber so that light enters the first optical fiber, wherein the first optical fiber is a multimode optical fiber having propagation modes;
   (b) inducing coupling among the propagation modes of the light in the first optical fiber;
   (c) coupling an output face of the first optical fiber to input faces of multiple individual second optical fibers in a multi-fiber bundle, wherein each output face of the individual fibers emits substantially similar light; and
   (d) detecting one or more analytes carried by a fluid with the light emitted from at least one of the second optical fibers.

19. A system providing multiple substantially similar secondary light sources for use in an optical detection system comprising:
   (a) a first optical fiber having an input face an output face, wherein the first optical fiber is a multimode optical fiber having propagation modes; wherein the first optical fiber is positioned so that coupling is induced among the propagation modes;
   (b) a primary light source for illuminating the input face of the first optical fiber so that light enters the first optical fiber; and (c) a plurality of secondary optical fibers, each second optical fiber having an input face and an output face; wherein each input face of the secondary optical fibers is coupled to the output face of the first optical fiber; wherein each output face of the secondary optical fibers emits substantially similar light; and wherein the light emitted from one or more of the secondary optical fibers can be used as a light source to detect one or more properties of one or more fluids.

20. The system of claim 14, 16 or 17 comprising means for monitoring the qualities of the light imaged onto the input face of the first optical fiber.

21. The system of claim 14 wherein the light from the primary light source entering the first optical fiber is substantially incoherent.

22. The system of claim 14 wherein the light from the primary light source entering the first optical fiber is substantially coherent.

23. The system of claim 14 wherein the light from the primary light source entering the first optical fiber is continuous.

24. The system of claim 14 wherein the light from the primary light source entering the first optical fiber is pulsed.

25. The system of claim 14 wherein at least a portion of one of the secondary optical fibers is directed to a substrate.

26. The system of claim 14, 16 or 17 wherein at least one of the secondary optical fibers is a multimode fiber.

27. The system of claim 14 wherein at least one of the secondary optical fibers is a single mode fiber.

28. The system of claim 14 comprising a light detector, wherein light emitted from one of the secondary optical fibers is directed to the light detector so that qualities of the light emitted from the other secondary optical fibers can be monitored.

29. The system of claim 14 comprising a light detector, wherein light emitted from one of the secondary optical fibers is directed to the light detector so that qualities of the light imaged onto the input face of the first optical fiber can be monitored.

* * * * *